(12) United States Patent
Bercoff et al.

(10) Patent No.: US 12,226,260 B2
(45) Date of Patent: *Feb. 18, 2025

(54) METHOD AND DEVICE FOR MEASURING A MEAN VALUE OF VISCO-ELASTICITY OF A REGION OF INTEREST

(71) Applicant: SUPERSONIC IMAGINE, Aix-en-Provence (FR)

(72) Inventors: Jeremy Bercoff, Aix en Provence (FR); David Savery, Calas-Cabries (FR); Mickael Tanter, Bagneux (FR); Jean-Luc Gennisson, Cergy (FR); Mathias Fink, Meudon (FR); Claude Cohen-Bacrie, Ventabren (FR)

(73) Assignee: SUPERSONIC IMAGINE, Aix en Provence (FR)

(*) Notice: Subject to any disclaimer, the term of this patent is extended or adjusted under 35 U.S.C. 154(b) by 843 days.

This patent is subject to a terminal disclaimer.

(21) Appl. No.: 16/695,974

(22) Filed: Nov. 26, 2019

(65) Prior Publication Data
US 2020/0093465 A1 Mar. 26, 2020

Related U.S. Application Data

(63) Continuation of application No. 14/039,584, filed on Sep. 27, 2013, now Pat. No. 10,603,013, which is a
(Continued)

(51) Int. Cl.
*A61B 8/08* (2006.01)
*A61B 5/00* (2006.01)
(Continued)

(52) U.S. Cl.
CPC ............ *A61B 8/485* (2013.01); *A61B 5/0051* (2013.01); *A61B 8/08* (2013.01); *A61B 8/4483* (2013.01);
(Continued)

(58) Field of Classification Search
CPC ....... A61B 5/0051; A61B 8/08; A61B 8/4483; A61B 8/485; G01N 29/34; G01N 29/36;
(Continued)

(56) References Cited

U.S. PATENT DOCUMENTS 3,789,833 A * 2/1974 Bom .................... A61B 8/0858
600/447
3,996,792 A 12/1976 Kubota et al.
(Continued)

FOREIGN PATENT DOCUMENTS

CN 105877783 * 8/2016
EP 1800603 6/2007
(Continued)

OTHER PUBLICATIONS

Clarivate Analytics machine translation of CN 105877783. Accessed Sep. 22, 2022.*
(Continued)

*Primary Examiner* — Colin T. Sakamoto
*Assistant Examiner* — Andrew W Begeman
(74) *Attorney, Agent, or Firm* — Merchant & Gould P.C.

(57) ABSTRACT

A method for measuring a mean visco-elasticity value for a soft material using a single probe carrying at least one transducer includes inducing, in a constraint zone, at least one burst of mechanical vibrations in order to generate internal shear waves in the tissue propagating from the constraint zone into the tissue, measuring, with the transducer, transient tissue displacements in at least one first measurement zone in the tissue, the first measurement zone being located away from the constraint zone, and estimating a mean visco-elasticity of the region of the tissue situated between the constraint zone and the first measurement zone from the measured transient tissue displacements of the tissue in the first measurement zone.

12 Claims, 1 Drawing Sheet

Related U.S. Application Data continuation of application No. 12/599,260, filed as application No. PCT/IB2007/002746 on May 16, 2007, now Pat. No. 8,545,407.

(51) Int. Cl.

| | | |
|---|---|---|
| *A61B 8/00* | (2006.01) | |
| *G01N 29/34* | (2006.01) | |
| *G01N 29/36* | (2006.01) | |
| *G01N 29/44* | (2006.01) | |
| *G01S 7/52* | (2006.01) | |
| *G01S 15/89* | (2006.01) | |
| *G06T 7/00* | (2017.01) | |

(52) U.S. Cl.
CPC ............ *G01N 29/34* (2013.01); *G01N 29/36* (2013.01); *G01N 29/44* (2013.01); *G01S 7/52036* (2013.01); *G01S 7/52042* (2013.01); *G01S 15/8927* (2013.01); *G06T 7/0012* (2013.01)

(58) Field of Classification Search
CPC ... G01N 29/44; G06T 7/0012; G01S 15/8927; G01S 7/52036; G01S 7/52042
See application file for complete search history.

(56) References Cited

U.S. PATENT DOCUMENTS

| | | |
|---|---|---|
| 4,043,181 A | 8/1977 | Nigam |
| 5,115,808 A | 5/1992 | Popovic et al. |
| 5,606,971 A | 3/1997 | Sarvazyan |
| 5,810,731 A | 9/1998 | Sarvazyan |
| 5,895,362 A | 4/1999 | Elstrom et al. |
| 6,113,543 A | 9/2000 | Bonnefous |
| 6,135,957 A | 10/2000 | Cohen-Bacrie |
| 6,168,572 B1 | 1/2001 | Vexler et al. |
| 6,494,840 B1 | 12/2002 | Mak et al. |
| 6,511,427 B1 | 1/2003 | Sliwa, Jr. |
| 6,558,324 B1 | 5/2003 | Von Behren |
| 6,770,033 B1 | 8/2004 | Fink et al. |
| 7,112,173 B1 | 9/2006 | Kantorovich |
| 7,553,283 B2 | 6/2009 | Sandrin et al. |
| 7,578,789 B2 | 8/2009 | Sandrin et al. |
| 7,632,232 B2 | 12/2009 | Lewandowski |
| 7,753,847 B2 | 7/2010 | Greenleaf |
| 7,892,188 B2 | 2/2011 | Walker |
| 8,328,736 B2 | 12/2012 | Varghese et al. |
| 8,347,692 B2 | 1/2013 | Sinkus |
| 8,545,407 B2 | 10/2013 | Bercoff |
| 10,603,013 B2 | 3/2020 | Bercoff |
| 10,795,007 B2 | 10/2020 | Bercoff |
| 2002/0010398 A1 | 1/2002 | Bonnefous |
| 2004/0167403 A1* | 8/2004 | Nightingale ......... A61B 5/0053 600/437 |
| 2004/0225215 A1 | 11/2004 | Querleux et al. |
| 2005/0004466 A1 | 1/2005 | Hynynen |
| 2005/0015009 A1 | 1/2005 | Mourad |
| 2005/0101867 A1 | 5/2005 | Johnson |
| 2005/0113691 A1 | 5/2005 | Liebschner |
| 2005/0119568 A1 | 6/2005 | Salcudean et al. |
| 2005/0154306 A1 | 7/2005 | Burcher |
| 2005/0251042 A1 | 11/2005 | Sandrin et al. |
| 2005/0252295 A1* | 11/2005 | Fink ..................... G01S 7/52042 73/603 |
| 2005/0288580 A1 | 12/2005 | Lagrange |
| 2006/0010964 A1 | 1/2006 | Sparks et al. |
| 2006/0074315 A1 | 4/2006 | Liang |
| 2007/0006651 A1 | 1/2007 | Kruger et al. |
| 2007/0016037 A1 | 1/2007 | Houle |
| 2007/0038095 A1 | 2/2007 | Greenleaf et al. |
| 2007/0112267 A1 | 5/2007 | Maatsumura |
| 2008/0249408 A1 | 10/2008 | Palmeri et al. |
| 2009/0005682 A1 | 1/2009 | Fan et al. |
| 2009/0124901 A1 | 5/2009 | Fink et al. |
| 2009/0143675 A1 | 6/2009 | Suzuki et al. |
| 2009/0149750 A1 | 6/2009 | Matsumura |
| 2009/0198130 A1 | 8/2009 | Osaka |
| 2009/0275834 A1 | 11/2009 | Watanabe et al. |
| 2010/0160778 A1 | 6/2010 | Eskandari et al. |
| 2010/0168566 A1 | 7/2010 | Bercoff |
| 2010/0170342 A1 | 7/2010 | Sinkus |
| 2010/0222678 A1 | 9/2010 | Bercoff |
| 2011/0046487 A1 | 2/2011 | Shin et al. |
| 2011/0054314 A1 | 3/2011 | Tanigawa et al. |
| 2011/0306884 A1 | 12/2011 | Tanigawa et al. |
| 2011/0319756 A1 | 12/2011 | Zheng et al. |
| 2014/0081138 A1 | 3/2014 | Bercoff |
| 2017/0224308 A1 | 8/2017 | Labyed et al. |
| 2020/0060653 A1* | 2/2020 | Kong ...................... A61B 8/14 |
| 2021/0033713 A1 | 2/2021 | Bercoff |

FOREIGN PATENT DOCUMENTS

| | | |
|---|---|---|
| FR | 2791136 | 9/2000 |
| FR | 2844058 | 3/2004 |
| JP | 8191834 | 7/1996 |
| JP | 2005533320 | 11/2005 |
| WO | WO 97/25921 | 7/1997 |
| WO | 2004/010380 | 1/2004 |
| WO | WO 2004/021888 | 3/2004 |

OTHER PUBLICATIONS

Barannik et al., "The influence of viscosity on the shear strain remotely induced by focused ultrasound in viscoelastic media", The Journal of the Acoustical Society of America, 115(5), 2358-2364. (2004).

Bercoff et al., "Supersonic Shear Imagining: A New Technique for Soft Tissue Elasticity Mapping," IEEE Transactions on Ultrasonics Ferroelectrics and Frequency Control, IEEE Service Center, vol. 51, No. 4, Apr. 2004, pp. 396-409.

Catheline et al., "Measurement of viscoelastic properties of homogeneous soft solid using transient elastography: An inverse problem approach", The Journal of the Acoustical Society of America, 116(6), 3734-3741. (2004).

Chen et al. "Quantifying elasticity and viscosity from measurement of shear wave speed dispersion", The Journal of the Acoustical Society of America 115.6 (2004): 2781-2785.

Sandrin et al., "Shear Elasticity Probe for Soft Tissues with 1-D Transient Elastography", IEEE Transactions on Ultrasonics, Ferroelectrics and Frequency Control, IEE USE, vol. 49, No. 4, Apr. 2002, pp. 436-446.

International Search Report for International Application No. PCT/IB2007/002746.

Bandyopadhyay et al., "Slow dynamics, aging, and glassy rheology in soft and living matter", Solid State Communications, Oxford, GB vol. 139, No. Sep. 11-12, 2006 pp. 589-598.

Chan, Roger W. et al., "Viscoelastic shear properties of human vocal fold mucosa: Measurement methodology and empirical results", Journal of the Acoustical Society of America, AIP/Acoustical Society of America, Melville, NY, US, vol. 106, No. 4, Oct. 1999 pp. 2008-2021.

French Preliminary Search Report from French priority application FR 07 04535; Report dated Jan. 22, 2008, 3 pages.

PCT International Search Report from counterpart application No. PCT/FR08/51129; Report dated Jan. 20, 2009, 8 pages.

Robert, B. et al,. "A new rheological model based on fractional derivatives for biological tissues", IEEE Ultrasonics Symposium Oct. 3-6, 2006, 1033-1036.

Szabo, Thomas L et al., "A model for longitudinal and shear wave propagation in viscoelastic media", Journal of the Acoustical Society of America, AIP/Acoustical Society of America, Melville, NY, US, vol. 107, No. 5, May 2000, pp. 2437-2446.

Szabo, Thomas L. , "The Domain Wave Equations for Lossy Media Obeying a Frequency Power Law"; J. Acoust. Soc. Am., vol. 96, No. 1, Jul. 1994; pp. 491-500.

(56) References Cited

OTHER PUBLICATIONS

Waters, Kendall R. et al., "On a Time-domain Representation of the Kramers-Kronig Dispersion Relations", J. Acoust. Soc. Am., vol. 106, No. 5, Pt. 1, Nov. 2000; pp. 2114-2119.
Waters, Kendall R. et al., "On the Applicability of Kramers-Kronig Relations for Ultrasonic Attenuation Obeying a Frequency Power Law", J. Acoust. Soc. Am., vol. 108, No. 2, Aug. 2000; pp. 556-563.
Bercoff J et al. "Study of Viscous and Elastic Properties of Soft Tissues Using Supersonic Shear Imaging", 2003 IEEE Ultrasonics Symposium Proceedings, vol. 1 of 2, Oct. 2003, 4 pages.
Canadian Office Action for related Canadian Patent Application No. 2,647,283 dated Nov. 12, 2013, 3 pages.
European Office Action for related European Patent Application No. 07727241.7 dated Apr. 21, 2009, 5 pages.
European Office Action for related European Patent Application No. 07727241.7 dated Feb. 2, 2010, 5 pages.
Japanese Office Action for related Japanese Patent Application No. 2009-502039 dated Dec. 6, 2011, 4 pages.
Nightingale et al. "Acoustic remote palpation: initial in vivo results", Ultrasonics Symposium, vol. 2, Oct. 2000, 6 pages.
Nightingale et al. "On the feasability of remote palpation using acoustic radiation force"; J. Acoust. Soc. Am. 110 (1), Jul. 2001, 10 pages.
PCT International Search Report for International Application No. PCT/EP07/052767, mailed Aug. 3, 2007, 3 pages.

\* cited by examiner

METHOD AND DEVICE FOR MEASURING A MEAN VALUE OF VISCO-ELASTICITY OF A REGION OF INTEREST

CROSS-REFERENCE TO RELATED APPLICATIONS

This continuation application claims the benefit of application Ser. No. 14/039,584 filed on Sep. 27, 2013 and entitled "Method and Device for Measuring a Mean Value of Visco-Elasticity of a Region of Interest" which in turn is a continuation application of application Ser. No. 12/599,260, filed on Nov. 6, 2009 and entitled "Method and Device for Measuring a Mean Value of Visco-Elasticity of a Region of Interest", which claims the benefit of PCT/IB2007/002746 filed May 16, 2007 and entitled "Method and Device for Measuring a Mean Value of Visco-Elasticity of a Region of Interest", and the entire contents of each of these applications are expressly incorporated herein by reference thereto.

FIELD OF THE INVENTION

The present invention relates to a method for measuring soft tissue mechanical properties.

The invention applies particularly to measuring a mean elasticity value for a soft material, like a biological tissue.

BACKGROUND OF THE INVENTION

Elastography techniques are devoted to measure biological tissues mechanical properties, as for example elasticity, in order to help medical diagnosis. Usually, they are implemented in medical imaging systems as additional feature of an existing imaging modality such as MRI or ultrasound.

In this context, elastography gives new clinical information to the physician to help him in establishing a diagnosis.

Several elastography techniques have been developed. Some are currently in evaluation and some are already embedded in a medical imaging product.

Schematically, elastography techniques can be divided into three different types: static, monochromatic or transient based techniques, depending on the characteristics of the mechanical excitation applied.

The present invention relates to transient elastography techniques that rely on the generation of a transient mechanical excitation in the body in order to deduce tissue mechanical properties.

Such methods can be classified according to the way this transient vibration is applied, externally, for example with a specific external device generating vibration, or internally, for example using the vibration generated by focalization of ultrasounds in a tissue resulting in an ultrasound radiation force.

Such methods can also be classified according to the imaging method, ultrasound or Magnetic Resonance Imaging for example.

All those elastography methods are imaging techniques in the sense that they define a continuous region of interest (ROI) in which imaging is performed in all this ROI and only in this ROI.

Indeed several local estimations tissue mechanical properties performed to give a viscoelastic map or elastogram in said predefined region of interest (ROI).

Usually those imaging techniques are time and processing consuming. Most of the time, they require huge amount of energy deposit in the tissue.

For those reasons they have not being implemented to date in real time on a medical imaging device.

Elastographic techniques are thus used punctually, for example once a lesion was located.

Nevertheless, in some cases, it is interesting to the physician to have a global and fast estimation of viscoelastic parameters of the ROI in an imaged tissue.

Such viscoelastic parameters enable to qualify the global mechanical behavior of the tissue.

Interesting applications concern pathologies inducing smooth spatial variations of the elasticity and are, for example, liver fibrosis evaluation, vascular diseases evaluation or muscles elasticity monitoring.

Such global information can also be very useful as a preliminary or calibration step to the imaging techniques cited above.

Today, only one ultrasound based technique proposing a global fast elasticity estimation of tissues is known from the document FR 2 791 136.

This technique is based on the concept of reducing the imaged region of interest to one ultrasound beam, imaging a shear wave propagation along the beam line and deducing a mean elasticity value along that line.

However such technique suffers from a major drawback.

It relies on the hypothesis that the elasticity value estimated along the single ultrasound line is a good and robust representation of the mean elasticity of the whole tissue.

This is usually not the case and such assumption leads to low performance regarding the statistical variance and the reproducibility of the measures.

It is thus challenging, with this technique, to distinguish early stage liver cirrhosis.

As a consequence there is a need for an Elastography technique able to measure a mean elasticity value of a given tissue without imaging the whole tissue and without making any assumption on the viscoelastic homogeneity of the tissue.

OBJECTS AND SUMMARY OF THE INVENTION

The present invention enables the above-mentioned drawbacks to be solved.

To this end, the invention provides a method for measuring a mean visco-elasticity value for a soft material, said method using a single probe carrying at least one transducer array and comprising the steps of:
a) inducing, in a constraint zone, at least one burst of mechanical vibrations with said transducer array in order to generate internal shear waves in the tissue propagating from said constraint zone into the tissue,
b1) measuring, with said transducer array, the transient tissue displacements in at least one first measurement zone in the tissue, said first measurement zone being located away from said constraint zone,
c) estimating a mean visco-elasticity of the region of the tissue situated between the constraint zone and the first measurement zone from said measured transient tissue displacements of the tissue in the first measurement zone.

By generating propagation of shear waves while performing only a measure in a measurement zone away from said constraint zone, it is rendered possible to know the result of the propagation of the shear waves in an extended region of the tissue situated between said constraint zone and said measurement zone. The displacements measured in the measurement zone are effectively dependent on the elasticity of this whole region in which the shear wave has propagated even if details of this elasticity are not available. A mean elasticity characteristic is thus deduced from said transient measurements.

Said invention is particularly adapted for measuring a mean visco-elasticity of biological tissue.

By "single probe" it is understood a device comprising one or a given number of transducer(s) able to generate waves and, eventually, grouped in a fixed configuration.

According to a variant, said method includes the following additional step b2) and the following modified step c'):

b2) measuring, with at least one second transducer, the transient tissue displacements in at least a second measurement zone in the tissue, said second measurement zone being located away from said constraint zone and from said first measurement zone, c') estimating a mean visco-elasticity of the region of the tissue situated between the two measurement zones from said measured transient tissue displacements of the tissue in the two measurement zones.

The use of two measurement zones enables to characterize the mean visco-elasticity of the region situated between the two measurement zones by using the transient measurements in the both measurement zones and by correlating them.

Thus, according to an advantageous characteristic, the estimation step implements a temporal comparison of the transient tissue displacements measured in said measurement zones using any conventional signal processing techniques for motion and distortion estimation.

Used signal processing techniques are such as intercorrelation, phase detection techniques, dispersion curves etc.

According to the invention, the transient tissue displacements may be known from at least a mechanical parameter included in the group formed by: shear wave group velocity, shear wave phase velocity, shear wave attenuation, shear viscosity and shear elastic modulus.

According to a specific characteristic, the region of the tissue where a mean viscoelasticity is estimated is considered as including said constraint zone.

According to a similar other characteristic, the region of the tissue where a mean visco-elasticity is estimated is considered as including said measurement zone(s).

According to an implementation, said mechanical vibration is induced by a biological source of mechanical displacement or by an external vibrator.

Said mechanical vibration can thus be generated by a natural source or by an artificial one.

According to an advantageous implementation, mechanical vibration is induced by ultrasonic radiation pressure in the tissue, said constraint zone being substantially a constraint line.

Ultrasounds are particularly adapted for generating a radiation pressure force within a tissue, said force inducing a movement in the tissue and thus the propagation of a shear wave.

According to an advantageous characteristic, said measuring step implements ultrasonic waves, said measurement zone being substantially a measurement line.

Such a feature is well known in the field of elastography where the propagation of the shear wave is followed by sending ultrasound on displacing structures and exploiting echoes on said displacing structures.

Advantageously, said constraint line is parallel to said measurement line.

According to a preferred implementation, said measurement line is located laterally away from said constraint line or from the other measurement line of a distance $R.\lambda$, $R$ being a real greater or equal to 2 and $\lambda$ being the wavelength of waves used to measure the tissue displacements.

Such a characteristic define a sufficient size for a region where a mean visco-elasticity is estimated. It defines a region where the propagating shear waves are different enough from the constraint zone and the measurement zone or from a first measurement zone to another in order to characterize said mean visco-elasticity.

The mean visco-elasticity measure is deduced from the velocity of the shear wave between the line of the burst and the line on which measures are performed or between the two lines of a pair of lines on which measures are performed. Such lines may be vertical or leaned.

According to an advantageous additional characteristic, said method further comprises a detection step for detecting the shear wave propagation in at least one measurement zone, said detection step automatically triggering an inducing step a).

This feature enables to optimize the induction of burst(s) in relation with the measurement of the propagation characteristic of the previously generated shear wave. Actually, the limited number of measures of transient tissue displacements for each propagated shear wave enables to realize continuous refreshing estimation of the mean visco-elasticity of the scanned tissue. This is original and new feature accessible thanks to the invention.

It also enables to adapt the time separation between two bursts to the characteristic of the tissue that is scanned.

Advantageously, said detection is realized using the detection of a maximum of intensity that can be a displacement peak for at least one point of the measurement zone at a predetermined depth.

This maximum may be detected using an inter-correlation calculation.

Such an inter-correlation calculation enables to easily control the crossing of the lines by the shear wave and to determine the time of propagation between at least two lines.

Said method may further comprise an energy evaluation step for evaluating the energy induced in the tissue during a predetermined amount of time, said inducing step a) being triggered as a function of the evaluated energy.

This enables to limit the quantity of energy induced in the tissue in order to avoid tissue degradations. It is particularly important for biological tissue.

Typically, this feature enables to increase the time separation between two bursts avoiding a destructive effect of the energy induced in the tissue.

This feature can thus be used in combination with the previous one which controls the propagation of the shear wave between lines on which measurements are performed.

According to an implementation, the method comprises, when implemented with a non specific transducer array, a step of selecting a sample of at least one transducer of said transducer array in order to realize the measurement step b) by measuring the transient tissue displacements in the measurement zone.

Preferably, several transducers are selected in order to focus the measurement.

In this implementation with a non specific transducer array, said method advantageously further comprises a step of selecting a sample of at least one transducer of said transducer array in order to induce said inducing step a) by generating said burst.

Preferably, several transducers are selected in order to focus waves for inducing a great mechanical vibration enabling to generate a shear wave.

The two last additional characteristics enable to use any non specific transducer array in order to implement the method of the invention as soon as their behaviors can be separately controlled.

In a realization, the transducer array is an ultrasound transducer array.

The invention further relates to a device for measuring the mean visco-elasticity of a soft material comprising means for:

a) inducing, in a constraint zone, at least one burst of mechanical vibrations in order to generate internal shear waves in the tissue propagating from said constraint zone into the tissue, b1) measuring the transient tissue displacements in at least one first measurement zone in the tissue, said first measurement zone being located away from said constraint zone, c) estimating a mean visco-elasticity of the region of the tissue situated between the constraint zone and the first measurement zone from said measured transient tissue displacements of the tissue in the first measurement zone.

Such a device of the invention can use standard components as soon as they can be controlled in order to perform the functions according to the invention. Thus non specific transducer arrays can be used.

Said device is advantageously dedicated to the implementation of the invention and includes two transducers, one dedicated to induce the burst, and one dedicated to the measurement of the transient tissue displacements.

According to a variant, said device further comprises additional means for:

b2) measuring the transient tissue displacements in at least a second measurement zone in the tissue, said second measurement zone being located away from said constraint zone and from said first measurement zone, and modified means for e') estimating a mean visco-elasticity of the region of the tissue situated between the two measurement zones from said measured transient tissue displacements of the tissue in the two measurement zones.

Said device is advantageously dedicated to the implementation of the invention and includes three transducers, one dedicated to induce the burst, and the two others dedicated to the measurement of the transient tissue displacements.

Devices according to the two last embodiments are specific for the implementation of the invention and can be made at low cost while making it possible to perform global elasticity estimations very quickly and on-the-fly.

Furthermore, such dedicated devices are much compact that non specific transducer arrays or probes.

At last, the invention relates to a computer program for performing functions of measuring the mean visco-elasticity of a soft material according to a method of the invention.

BRIEF DESCRIPTION OF THE DRAWINGS

Other aspects and advantages of the present invention appear more clearly on reading the following description of particular embodiments, which description is given purely by way of non-limiting example and is made with reference to the accompanying drawings, in which.

MORE DETAILED DESCRIPTION

Figure 1:
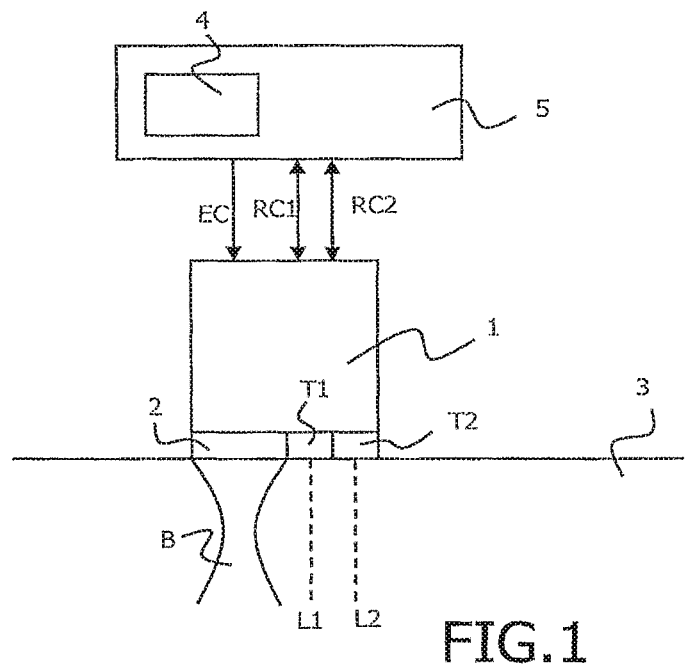
FIG. 1 shows a first embodiment of a measurement device in accordance with the present invention.

FIG. 1 shows a device 1 in accordance with a first embodiment of the invention. It consists in a so called "1D" probe including three transducers 2, T1 and T2.

First transducer 2 is dedicated to generate a shear wave in tissue 3.

It can be qualified as "pushing" transducer and works, for example at a central frequency of 3 MHz.

In such a case, it is designed to generate an ultrasound beam B, said beam B being advantageously of a few mm width and in a depth range between 2 and 6 cm.

Said ultrasound beam B can be of such a power that it can create a shear wave SW in the tissue 3.

The two other transducers T1 and T2 are imaging transducers dedicated to image the tissue 3 along two ultrasound lines L1 and L2. Said transducers T1 and T2 advantageously emit ultrasounds of central frequency 5 MHz. They are advantageously separated by 1-2 cm. Simultaneous or time-shifted emissions may be implemented.

Both ultrasound lines L1 and L2 are positioned in the vicinity of a region of interest for an elasticity measurement.

Said probe 1 is electronically controlled by one programmable emitting channel EC controlling the pushing element 2 and two programmable transmit/receive channels RC1 and RC2 controlling the imaging elements T1 and T2. Said transmit/receive channels are connected to at least one memory 4 available to store in real time data coming from the imaging channels RC1 and RC2.

Then, a processing is performed in real time on a computer having access to said memory 4 or on a dedicated processing system 5 including said memory 4 and connection to channels EC, RC1 and RC2.

The purpose of this processing is to achieve a mean visco-elasticity measurement for the region of interest.

For such a purpose, the probe 1 is placed on the surface of the tissue 3 to be investigated, such as liver muscles or artery walls. A high power ultrasound beam B, for example at 3 MHz, is generated by the pushing element 2 to create a shear wave SW in the tissue 3.

Then, the probe 1 is such that imaging transducers T1 and T2 send multiple pulses, for example at 5 MHz. These multiple pulses enable to track the induced displacements along the two ultrasound lines L1 and 12.

The pulses are sent at a PRF (for Pulse Repetition Frequency) high enough to correctly sample the medium transient response. Typically, PRF=1000 to 5000 Hz.

The use of lower frequency for the pushing sequence allows better pushing efficiency and less interference between pushing and imaging beams.

Such a measurement of displacements in a tissue is well known in the field of elastography and may be performed using any manner known to the person skilled in the art.

For example, processing consists in first applying motion estimation algorithms such as 1D cross correlation or Doppler based algorithms.

Tissue displacements or velocity V are then assessed along lines L1 and L2 as a function of time t: V1(z1,t) and V2(z2,t), where z1 et z2 are the respective depth along lines L1 and L2 and t is the time).

Displacement data is then used to deduce shear wave characteristics along the two lines L1 and L2 and then measure a global mechanical parameter of the medium located between the two lines L1 and L2. An example of mechanical parameter estimated is the speed $C_T$ of the shear wave between those two points:

$$c_T = \mathrm{argmax}_C \Sigma_{t,z2}(\Sigma_{z1} V_1(t,z_1))(\Sigma_{z2} V_2(t-d_{12}/C, z_2)),$$

where d12 is the distance between the two lines L1 et L2.

The depth of interest on which the displacement field are summed can be chosen to cover the depth of field or just a small range. In the second case, measurements can be repeated for different slices located at different depths. In this case, an estimated parameter $c_T(z)$ which is a function of depth is available.

This first embodiment of the invention presents the advantage of being particularly compact because of the basic association of only three transducers.

Figure 2:
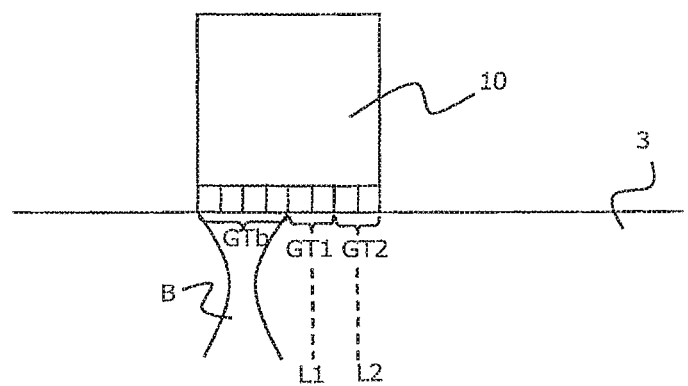
FIG. 2 shows a second embodiment of a measurement device in accordance with the present invention.

FIG. 2 shows a second embodiment of a measurement device in accordance with the present invention. It consists in an implementation of the method in an echographic imaging system using an ultrasound array probe 10 to image the tissue 3.

The following describes how a real time echographic system with mean visco-elasticity measurement and display is thus obtained.

Said echographic system is advantageously controlled in order to generate an ultrasound pushing beam B in the tissue 3.

As illustrated on FIG. 2, such beam B may be obtained by specific focusing of ultrasound emitted by a group GTb of transducers located on one of the sides of the transducer array 10.

Two other transducers or group of transducers GT1, GT2 are subsequently used to image two lines of interest L1 and L2.

Advantageously, first, a classical ultrasound imaging sequence is performed to compute an ultrasound image of the region of interest. This is an approximately 20 ms long step.

Then the global elasticity measurement method according to the invention is performed using an ultrasound pushing beam B and at least one tracking line L1 with the same probe 10 than the one used for ultrasound imaging. This is an approximately 20 ms long step.

Both sequences, ultrasound imaging and elasticity estimation, are then looped continuously to provide in real time both ultrasound images and global elasticity estimation to the user.

The elasticity value may be displayed on a side of the echographic image. This coupling appears very interesting as guidance for the physician to locate areas of pathological interest characterized by an increase of elasticity.

An alarm may also be emitted as soon as the estimated mean elasticity value reaches a predetermined threshold. The emitted sound warns the physician of the necessity of a more thorough investigation. This alarm feature may be implemented alone or in parallel with the displaying of the mean elasticity value.

A preferred use of the invention thus lies in the field of medical imaging, since it enables a fast preliminary scanning of elasticity characteristics of a region of interest. As elasticity abnormalities can reveal lesions, the method of the invention can help in localization and detection of illness.

What is claimed is:

1. A device for measuring velocity of shear waves in a biological tissue, comprising:
    a) an ultrasound beam generating transducer that exposes the biological tissue to an ultrasound beam in a constraint zone, the ultrasound beam generating internal shear waves in the biological tissue, the internal shear waves propagating in a first measurement zone which is outside the constraint zone;
    b) at least two imaging transducers for imaging tissue displacements in said first measurement zone in the tissue along at least two ultrasound lines, the at least two imaging transducers sending multiple pulses along the at least two ultrasound lines spaced apart from each other in the first measurement zone, wherein each of the imaging transducers is dedicated to image tissue displacement along a single respective one of the at least two ultrasound lines; and
    c) a processor for receiving signals from an imaging transducer from the imaging transducers corresponding to said image tissue displacements, said processor determining a velocity of the shear wave between the two ultrasound lines based on the tissue displacements.

2. A device according to claim 1, wherein the ultrasound beam generating transducer is dedicated to induce a burst that generates the internal shear waves, and the imaging transducer is dedicated to a measurement of the tissue displacements.

3. The device of claim 1, wherein the ultrasound beam generating transducer and the imaging transducer are included in a single probe.

4. The device of claim 1, further comprising a display configured to display an indication of the determined velocity of the shear wave.

5. The device of claim 1, wherein the ultrasound beam generating transducer is distinct from the at least two imaging transducers.

6. The device of claim 1, wherein the at least two ultrasound lines are parallel to each other.

7. A device for measuring velocity of shear waves in a biological tissue, comprising:
    a) an ultrasound beam generating transducer that exposes the biological tissue to an ultrasound beam in a constraint zone, the ultrasound beam generating internal shear waves in the biological tissue, the internal shear waves propagating in a first measurement zone and in a second measurement zone which are outside the constraint zone;
    b1) an imaging transducer for imaging tissue displacements in said first measurement zone along one of two ultrasound lines, the imaging transducer sending multiple pulses along the one of the ultrasound lines in the first measurement zone, wherein the imaging transducer is dedicated to image tissue displacement only along the one of the two ultrasound lines; and
    b2) a further imaging transducer for imaging tissue displacements in the second measurement zone located away from the constraint zone and along another one of the two ultrasound lines, the further imaging transducer sending multiple pulses along the other one of the ultrasound lines in the second measurement zone, wherein the further imaging transducer is dedicated to image tissue displacement only along the other of the two ultrasound lines; and
    c) a processor for receiving signals from the imaging transducer and the further imaging transducer, the received signals corresponding to said image tissue displacements, said processor determining a velocity of the shear wave between the two ultrasound lines based on the tissue displacements.

8. A device according to claim 7, wherein the ultrasound beam generating transducer is dedicated to induce a burst that generates the internal shear waves, and the imaging transducer and further imaging transducer are dedicated to a measurement of the tissue displacements.

9. The device of claim 7, wherein the ultrasound beam generating transducer, the imaging transducer, and the further imaging transducer are included in a single probe.

10. The device of claim 7, further comprising a display configured to display an indication of the determined velocity of the shear wave.

11. The device of claim 7, wherein the ultrasound beam generating transducer is distinct from both the imaging transducer and the further imaging transducer.

12. The device of claim 7, wherein the two ultrasound lines are parallel to each other.

* * * * *

UNITED STATES PATENT AND TRADEMARK OFFICE
CERTIFICATE OF CORRECTION

PATENT NO. : 12,226,260 B2
APPLICATION NO. : 16/695974
DATED : February 18, 2025
INVENTOR(S) : Bercoff et al.

It is certified that error appears in the above-identified patent and that said Letters Patent is hereby corrected as shown below:

In the Specification

Column 1, Line 39, after "in" insert -- clinical --;

Column 1, Line 62, after "estimations" insert -- of --; and

Column 1, Line 63, before "performed" insert -- are --.

Column 3, Line 39, "viscoelasticity" should read -- visco-elasticity --.

Column 5, Line 40, "e')" should read -- c') --.

Column 6, Line 47, "12" should read -- L2 --.

Signed and Sealed this
Eighth Day of April, 2025

Coke Morgan Stewart
*Acting Director of the United States Patent and Trademark Office*